(12) United States Patent
Velati et al.

(10) Patent No.: US 7,872,137 B2
(45) Date of Patent: Jan. 18, 2011

(54) PROCESS FOR THE PREPARATION OF MIVACURIUM CHLORIDE

(75) Inventors: Maurizio Francesco Velati, Mezzana Rabattone (IT); Andrea Busca, Vigevano (IT); Cristina Manfrotto, Gropello Cairoli (IT); Marco Nicolini, Belgioioso (IT); Claudio Gianluca Pozzoli, Monza (IT)

(73) Assignee: Farmabios S.p.A., Gropello Cairoli (IT)

( * ) Notice: Subject to any disclaimer, the term of this patent is extended or adjusted under 35 U.S.C. 154(b) by 865 days.

(21) Appl. No.: 11/820,374

(22) Filed: Jun. 19, 2007

(65) Prior Publication Data

US 2007/0293534 A1    Dec. 20, 2007

Related U.S. Application Data

(60) Provisional application No. 60/815,227, filed on Jun. 20, 2006.

(51) Int. Cl.
*C07D 401/02* (2006.01)
(52) U.S. Cl. .................................................. 546/140
(58) Field of Classification Search ..................... None
See application file for complete search history.

(56) References Cited

U.S. PATENT DOCUMENTS 4,761,418 A    8/1988    Swaringen, Jr. et al. ...... 514/308

OTHER PUBLICATIONS

Tuba et al. "Synthesis and Structure-Activity Relationships of Neuromuscular Blocking Agents," Current Medicinal Chemistry, vol. 9, No. 16, Aug. 2002 (Abstract Only).

*Primary Examiner*—Zinna N Davis
(74) *Attorney, Agent, or Firm*—Ohlandt, Greeley, Ruggiero & Perle, L.L.P.

(57) ABSTRACT

A process for preparing the [R—[R*,R*-(E)]]-2,2'-(1,8-dioxo-4-octene-1,8-diyl) bis(oxy-3,1-propanediyl)bis(1,2,3,4-tetrahydro-6,7-dimethoxy-2-methyl-1-[(3,4,5-trimethoxyphenyl) methyl]isoquinolinium) dichloride, commonly known as mivacurium chloride, useful as short-duration neuromuscular blocking agent.

19 Claims, No Drawings

PROCESS FOR THE PREPARATION OF MIVACURIUM CHLORIDE

CROSS-REFERENCED APPLICATIONS

The present disclosure claims priority to US Provisional Application No. 60/815,227, filed on Jun. 20, 2006, which is incorporated herein by reference in its entirety.

BACKGROUND

1. Field of the Invention

The present invention refers to a process for preparing the [R—[R*,R*-(E)]]-2,2'-(1,8-dioxo-4-octene-1,8-diyl) bis(oxy-3,1-propanediyl) bis(1,2,3,4-tetrahydro-6,7-dimethoxy-2-methyl-1-[(3,4,5-trimethoxyphenyl)methyl]isoquinolinium)dichloride, commonly known as mivacurium chloride, having the following formula:

carbon atoms and, at each center, may therefore exist either the R or the S configuration. Moreover, the methyl substituents on each of the two quaternary nitrogen atoms may exist in either the R or the S configuration.

The compound having the R configuration at both chiral centers is known to be free from significant side effects at the normal dosages. In view of what explained above, this compound may exist in three diastereoisomers: the trans-trans (1R, 1'R; 2S, 2'S); the cis-trans (1R, 1'R; 2R, 2'S), and the cis-cis diastereoisomer (1R, 1'R; 2R, 2'R). The trans-trans and the cis-trans diastereoisomers have neuromuscolar blocking potencies not significantly different from each other, whereas the cis-cis diastereoisomer has been estimated to have approximately one tenth the neuromuscolar blocking potency of the other two diastereoisomers.

Mivacurium chloride has been disclosed for the first time in U.S. Pat. No. 4,761,418, together with a process for preparing

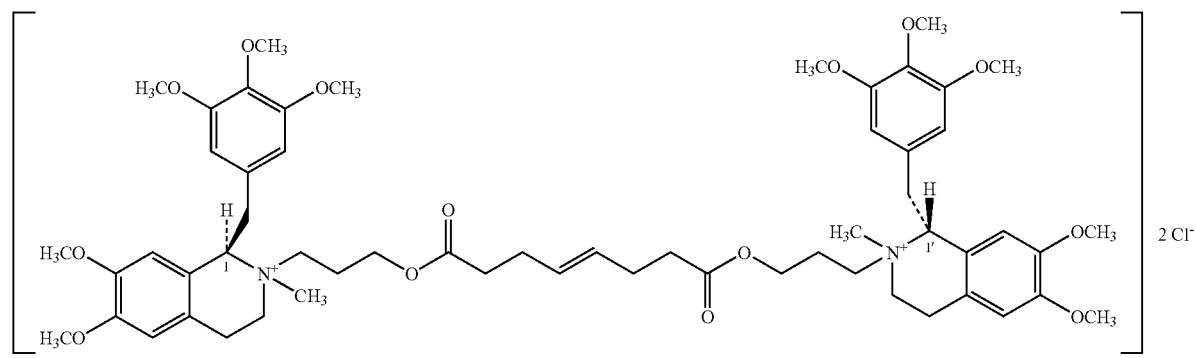

2. Discussion of the Background Art

Mivacurium chloride is a rapid, non-depolarising, neuromuscular blocking agent of short duration, used therefore as anesthetic, to provide skeletal muscle relaxation in minor surgical operations, in emergency surgical procedures of short to intermediate duration and during intubation of the trachea.

As it is evident from the formula above reported, mivacurium chloride contains a chiral center at the C(1) and C(1')

it. As far as the Applicant is aware, the process disclosed in U.S. Pat. No. 4,761,418 is the only process for the preparation of mivacurium chloride known in the art, and it consists in the coupling of (E)-4-octene-1,8-dioic acid dichloride with the isochinolinic derivative of formula (A), hereinafter referred to as compound A and whose chemical name is N-3-hydroxypropyl-1-(R)-5'-methoxylaudanosinium chloride, in warm 1,2-dichloroethane:

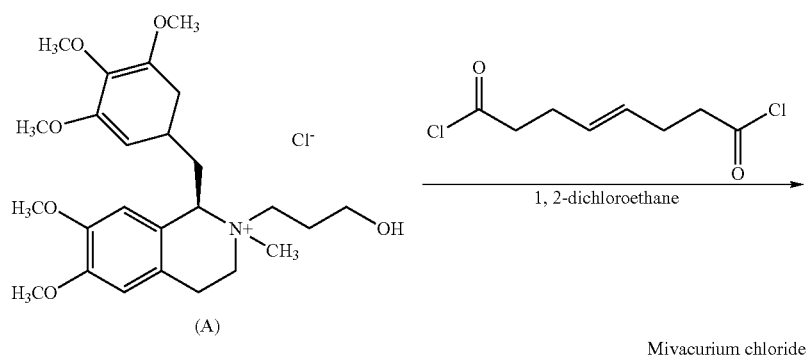

(A)                    Mivacurium chloride

According to U.S. Pat. No. 4,761,418, once the coupling reaction is complete, the solvent is removed by distillation under vacuum and replaced by chloroform. The so obtained chloroformic solution is then washed with diluted aqueous solutions of sodium chloride to eliminate the isochinolinic compound A in excess, and the organic solvent is removed by distillation under vacuum, thus obtaining an amorphous solid. This solid product is then purified from impurities by washings with warm 2-butanone, removing then the residual organic solvent by distillation under vacuum. Finally, the amorphous solid product is dissolved in methanol, filtered and freeze-dried, thus yielding the mivacurium chloride.

Substantially the same synthesis has been disclosed also in *Current Medicinal Chemistry*, vol. 9, Nov. 16, 2002.

A fundamental limitation of this process consists in that the raw product obtainable by the above said process contains a high amount of various impurities, mainly represented by the compound A used as starting material both as cis and trans diastereoisomer, and by the following product, so called "acid ester", both as cis and trans diastereoisomer:

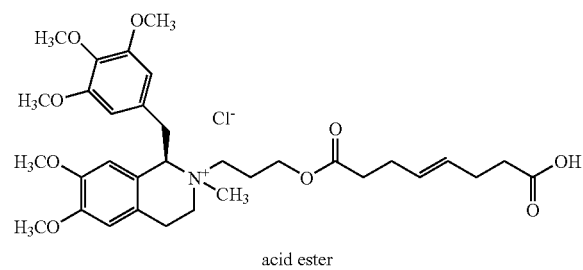

acid ester

Due to the pharmaceutical use of mivacurium chloride, it is of paramount importance to have available a process for the purification of this product. But the purification of the raw product in the form of an amorphous solid, as disclosed in U.S. Pat. No. 4,761,418, is difficult on the operational front: the amorphous solid to be treated with organic solvents is actually a gummy product, not miscible with the proposed organic solvent. Therefore, for this treatment to be efficacious, it must be repeated so many times that it is not economically practicable, and cannot be scaled up.

It is therefore still felt the need of developing a scalable process for preparing mivacurium chloride having a high purity degree, that does not show the drawbacks highlighted above for the known process.

SUMMARY

Now the Applicant has developed a process for preparing mivacurium chloride having a higher purity degree, which is cost-effective and easily scalable.

Subject of the present invention is therefore a process for the preparation of mivacurium chloride having a purity degree higher than 97.5%, said process comprising the following steps:

(i) coupling of N-3-hydroxypropyl-1-(R)-5'-methoxy-laudanosinium chloride with (E)-4-octene-1,8-dioic acid dichloride, in a suitable organic solvent, to obtain raw mivacurium chloride;

(ii) extraction of raw mivacurium chloride with water;

(iii) treatment of the aqueous solution of raw mivacurium chloride with a suitable nonionic polymeric adsorbent resin insoluble in water; and (iv) recovery from the aqueous solution of step iii) of mivacurium chloride having a purity degree higher than 97.5%.

Further subject of the present invention is the mivacurium chloride obtainable by the above said process, in which said mivacurium chloride has a purity degree higher than 97.5%.

Further subjects of the invention are a pharmaceutical composition containing the mivacurium chloride obtainable by the above said process in an effective neuromuscular relaxant amount, optionally in combination with pharmaceutically acceptable excipients and/or diluents; and a method for producing neuromuscular relaxation in a patient in need thereof, comprising administering to said patient an effective neuromuscular relaxant amount of the mivacurium chloride obtainable by the above said process.

Features and advantages of the present invention will be illustrated in detail in the following description.

DETAILED DESCRIPTION OF THE PREFERRED EMBODIMENT

According to the present invention, by the expression "purity degree" is meant the sum of the three HPLC areas in percentage, corresponding to the three diastereoisomers of mivacurium chloride: the trans-trans (1R, 1'R; 2S, 2'S); the cis-trans (1R, 1'R; 2R, 2'S), and the cis-cis diastereoisomer (1R, 1'R; 2R, 2'R).

As the suitable organic solvent in step i), dichloromethane is preferably used.

The starting N-3-hydroxypropyl-1-(R)-5'-methoxy-laudanosinium chloride in step i) may be for example in the form of trans diastereoisomer, or in the form of a diastereoisomeric mixture wherein the trans:cis ratio is higher than 2.3:1, and preferably equal to 3:1.

The starting (E)-4-octene-1,8-dioic acid dichloride is prepared starting from commercially available products according to procedures known to any skilled persons; for example it can be prepared by reacting (E)-4-octene-1,8-dioic acid with tionyl chloride, as described in the following examples.

The extraction of raw mivacurium chloride in step ii) may be carried out directly by adding water to the solution in the organic solvent coming from step i); or in the alternative, by evaporating the organic solvent of the solution coming from step i) to obtain an amorphous solid, which is then re-dissolved in a suitable organic solvent, preferably dichloromethane, and the so obtained solution washed with aqueous solutions of suitable inorganic salts, selected from the group consisting of sodium chloride, ammonium chloride and calcium chloride.

According to a preferred embodiment of the present process, the treatment with the resin in step iii) is carried out at room temperature and, as a suitable nonionic polymeric adsorbent resin insoluble in water, the resin known with the trade name Amberlite® XAD-4 is preferably used; this commercial product has as the main features a particle mean size ranging from 0.49 to 0.69 mm, a porosity $\geq$0.50 ml/ml and a chemical structure that is a macroreticular cross-linked polymeric matrix with the following repeating unit:

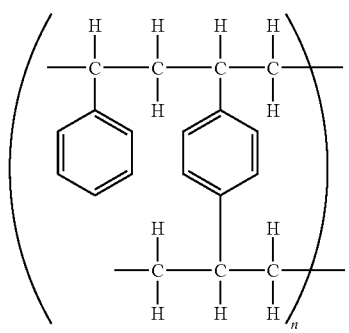

The treatment in step iii) may be carried out by adding the resin to the aqueous solution containing the raw mivacurium chloride, and maintaining the resulting mixture under stirring for a reaction time comprised between 2 and 24 hours; or, in the alternative, it may be carried out by passing the aqueous solution through a column packed with the resin and using water as the eluent.

According to the first embodiment, the resin is added to the aqueous solution, at once or by portions, in a total amount comprised between 0.2 and 20 parts by weight per 1 part by weight of the starting N-3-hydroxypropyl-1-(R)-5'-methoxy-laudanosinium chloride made to react in step i). Preferably a total amount of 0.5 parts by weight per 1 part by weight of the starting N-3-hydroxypropyl-1-(R)-5'-methoxy-laudanosinium chloride is added to the aqueous solution by two portions staggered by 20 hours.

According to the second embodiment, the resin is used in an amount comprised between 10 and 40 parts by weight, and preferably equal to 20 parts, per 1 part by weight of the starting N-3-hydroxypropyl-1-(R)-5'-methoxy-laudanosinium chloride made to react in step i).

According to the present process, the recovery of pure mivacurium chloride in step iv) may be carried out on the aqueous solution coming from step iii) for example by a technique selected from the group consisting of freeze-drying, spray-drying and extraction in a suitable organic solvent. This extraction may be carried out by first adding to said aqueous solution a suitable inorganic salt, extracting mivacurium chloride in dichloromethane, evaporating the dichloromethane obtaining an amorphous solid, dissolving said amorphous solid in methanol, evaporating the methanol obtaining an amorphous solid, and optionally adding a solvent in which mivacurium chloride is not soluble, preferably selected from the group consisting of ethyl ether, diisopropyl ether and methyl t-butyl ether.

The present process is able to yield mivacurium chloride having a far higher purity degree than the product obtainable by the known prior art process. Furthermore, the present process allows to obtain this product from a aqueous solution, so that the recovery of the final product in step iv) may be carried out by freeze-drying from water instead of from an organic solvent, or by means of spray-drying technique.

The present mivacurium chloride prepared as described above, may be used for preparing pharmaceutical compositions useful as neuromuscular relaxant, preferably for parenteral administration in the form of solutions or in the form of freeze-dried solids to be reconstituted with water or other suitable solvents at the time of use. The present compositions may also comprise one or more pharmaceutically acceptable excipients and/or diluents.

The following examples are reported as a non limiting illustration of the invention.

Example 1

Comparison

Preparation of Mivacurium Chloride According to U.S. Pat. No. 4,761,418

Thionyl chloride (2 ml) and (E)-4-octene-1,8-dioic acid (0.41 g) are made to react at reflux temperature until reaction is complete. Thionyl chloride in excess is evaporated under vacuum, while the residue of (E)-4-octene-1,8-dioic acid dichloride is diluted with dichloromethane.

The so obtained solution is added, drop by drop and at room temperature, while protecting from moisture, to a solution prepared dissolving in dichloromethane N-3-hydroxypropyl-1(R)-5'-methoxylaudanosinium chloride (2.5 g; mixture trans:cis approximately 3:1 as determined by HPLC).

After 18 hours, the solvent is evaporated under vacuum, thus obtaining an amorphous solid product, which is dissolved in dichloromethane (30 ml). The so obtained solution is washed with an aqueous solution of sodium chloride 5% (4×35 ml); dichloromethane is then removed by evaporation of the solution under vacuum, obtaining a gummy solid product, which is then suspended in methyl ethyl ketone (40 ml). The so obtained suspension is heated up to reflux temperature, then cooled down to room temperature. The surnatant is then removed with a syphon, whereas the gummy residue is washed with methyl ethyl ketone (5×40 ml), then subjected to HPLC analysis, yielding the following results: 56.2% (mivacurium chloride trans-trans), 34.1% (mivacurium chloride cis-trans), 5.3% (mivacurium chloride cis-cis), 2.1% (acid ester trans), 1.0% (acid ester cis), 0.3% (compound A trans), not detected (compound A cis), 0.8% (other impurities).

After last washing methyl ethyl ketone is removed by evaporation under vacuum, and the solid product obtained is dissolved in methanol and treated with carbon before evaporation to dryness under vacuum. 0.8 g of mivacurium chloride having the above said composition and a purity degree of 95.6%, are thus obtained.

Example 2

Preparation of Mivacurium Chloride According to the Invention

Thionyl chloride (2 ml) and (E)-4-octene-1,8-dioic acid (0.41 g) are made to react at reflux temperature until reaction is complete. Thionyl chloride in excess is evaporated under vacuum, while the residue of (E)-4-octene-1,8-dioic acid dichloride is diluted with dichloromethane.

The so obtained solution is added, drop by drop and at room temperature, while protecting from moisture, to a solution prepared dissolving in dichloromethane N-3-hydroxypropyl,1-(R) 5'-methoxylaudanosinium chloride (2.5 g; mixture trans:cis approximately 3:1 as determined by HPLC).

After 18 hours, the solvent is evaporated under vacuum, thus obtaining an amorphous solid product, which is dissolved in dichloromethane (30 ml). The so obtained solution is washed with an aqueous solution of sodium chloride 5% (4×35 ml), dichloromethane is then removed by evaporation of the solution under vacuum, obtaining a gummy solid product, which is then dissolved in water (50 ml). To the so obtained solution the resin XAD-4 (20 g) is added under stirring at room temperature, maintaining stirring and temperature for 1.5 hours.

The resin XAD-4 is then removed by filtration and sodium chloride is added to the filtrate, thus obtaining a solution having a concentration of approximately 20%. Pure product is then extracted by repeated washings with dichloromethane: the organic phases are collected and concentrated by distillation under vacuum to obtain an amorphous solid product, which is dissolved in methanol, and treated with carbon before concentration to dryness under vacuum.

0.9 g of mivacurium chloride are so obtained, showing by HPLC analysis a purity degree of 98.8% and the following composition: 57.3% (mivacurium chloride trans-trans), 35.1% (mivacurium chloride cis-trans), 6.4% (mivacurium chloride cis-cis), 0.7% (acid ester trans), 0.2% (acid ester cis), 0.1% (compound A trans), not detected (compound A cis), 1.2% (other impurities).

Example 3

Preparation of Mivacurium Chloride According to the Invention

Thionyl chloride (2 ml) and (E)-4-octene-1,8-dioic acid (0.41 g) are made to react at reflux temperature until reaction is complete. Thionyl chloride in excess is evaporated under vacuum, while the residue of (E)-4-octene-1,8-dioic acid dichloride is diluted with dichloromethane.

The so obtained solution is added, drop by drop and at room temperature, while protecting from moisture, to a solution prepared dissolving in dichloromethane N-3-hydroxypropyl-1-(R)-5'-methoxylaudanosinium chloride (2.5 g; mixture trans:cis approximately 3:1 as determined by HPLC).

After 18 hours, the solvent is evaporated under vacuum, thus obtaining an amorphous solid product, which is dissolved in dichloromethane (30 ml). The so obtained solution is washed with an aqueous solution of sodium chloride 5% (4×35 ml), then dichloromethane is removed by evaporation of the solution under vacuum, obtaining a gummy solid product, which is then dissolved in water (50 ml). To the so obtained solution the resin XAD-4 (20 g) is added under stirring at room temperature, maintaining stirring and temperature for 1.5 hours.

The resin XAD-4 is then removed by filtration and the aqueous solution is freeze-dried, thus obtaining 1.0 g of mivacurium chloride having a purity degree of 97.9% and the following HPLC composition: 56.8% (mivacurium chloride trans-trans), 34.9% (mivacurium chloride cis-trans), 6.0% (mivacurium chloride cis-cis), 0.9% (acid ester trans), 0.3% (acid ester cis), 0.2% (compound A trans), not detected (compound A cis), 0.6% (other impurities).

Example 4

Preparation of Mivacurium Chloride According to the Invention

Thionyl chloride (11 ml) and (E)-4-octene-1,8-dioic acid (2.3 g) are made to react at reflux temperature until reaction is complete. Thionyl chloride in excess is evaporated under vacuum, while the residue of (E)-4-octene-1,8-dioic acid dichloride is diluted with dichloromethane.

The so obtained solution is added, drop by drop and at room temperature, while protecting from moisture, to a solution prepared dissolving in dichloromethane N-3-hydroxypropyl-1(R)-5'-methoxylaudanosinium chloride (14 g; mixture trans:cis approximately 3:1 as determined by HPLC).

After 18 hours, water is added to the reaction mixture, and the two phases are allowed to separate. The organic phase is then washed with water. The aqueous phases are collected and added with XAD-4 resin (3.5 g) maintaining the mixture under stirring at room temperature for approximately 12 to 16 hours. The resin XAD-4 is then removed by filtration and washed with water. To the filtrate further XAD-4 resin (3.5 g) is added, and the reaction mixture is maintained under stirring for approximately 6 to 8 hours. The resin is then removed by filtration and washed with water. To the filtrate sodium chloride is added until an almost saturated solution is obtained. Pure product is extracted by repeated washings with dichloromethane: the organic phases are collected and treated with an aqueous solution of sodium chloride 5%, the organic solution is then concentrated by distillation under vacuum until an amorphous solid is obtained, which is then dissolved in methanol, and treated with carbon before concentration to dryness under vacuum. The solid product is recovered by treatment with ethyl ether, filtration and evaporation under vacuum. 10 g of mivacurium chloride having a purity degree of 97.6% and the composition above reported, are obtained.

Example 5

Preparation of Mivacurium Chloride According to the Invention

Thionyl chloride (2 ml) and (E)-4-octene-1,8-dioic acid (0.41 g) are made to react at reflux temperature until reaction is complete. Thionyl chloride in excess is evaporated under vacuum, while the residue of (E)-4-octene-1,8-dioic acid dichloride is diluted with dichloromethane.

The so obtained solution is added, drop by drop and at room temperature, while protecting from moisture, to a solution prepared dissolving in dichloromethane N-3-hydroxypropyl-1-(R)-5'-methoxylaudanosinium chloride (2.5 g; mixture trans:cis approximately 3:1 as determined by HPLC).

After 18 hours, the solvent is evaporated under vacuum, thus obtaining an amorphous solid product, which is dissolved in dichloromethane (30 ml). The so obtained solution is washed with an aqueous solution of sodium chloride 5% (4×35 ml), then dichloromethane is removed by evaporation of the solution under vacuum, obtaining a gummy solid product, which is then dissolved in water (50 ml). The so obtained solution is passed through a column packed with the XAD-4 resin (40 g), using water as the eluent.

The fractions containing the pure product are collected and added with sodium chloride, so as to obtain a solution having a concentration of approximately 20%. The pure product is extracted by washings with dichloromethane: the organic phases are collected and concentrated by distillation under vacuum until an amorphous solid product is obtained; this product is then dissolved in methanol and the so obtained solution is treated with carbon before concentration to dryness under vacuum. 0.9 g of mivacurium chloride are obtained having a purity degree of 99.1% and the following composition determined by HPLC: 56.3% (mivacurium chloride trans-trans), 36.1% (mivacurium chloride cis-trans), 6.7% (mivacurium chloride cis-cis), 0.1% (acid ester trans), not detected (acid ester cis), 0.2% (compound A trans), 0.07% (compound A cis), 0.5% (other impurities).

What is claimed is:

1. A process for the preparation of mivacurium chloride having a purity degree higher than 97.5%, said process comprising the following steps:
   (i) coupling of N-3-hydroxypropyl-1-(R)-5'-methoxylaudanosinium chloride with (E)-4-octene-1,8-dioic acid dichloride, in a suitable organic solvent, to obtain raw mivacurium chloride;
   (ii) extraction of raw mivacurium chloride with water;
   (iii) treatment of the aqueous solution of raw mivacurium chloride with a suitable nonionic polymeric adsorbent resin insoluble in water; and
   (iv) recovery from the aqueous solution of step iii) of mivacurium chloride having a purity degree higher than 97.5%.

2. The process according to claim 1, wherein said suitable organic solvent in step i) is dichloromethane.

3. The process according to claim 1, wherein said N-3-hydroxypropyl-1-(R)-5'-methoxylaudanosinium chloride in step i) is in the form of trans diastereoisomer.

4. The process according to claim 1, wherein said N-3-hydroxypropyl-1-(R)-5'-methoxylaudanosinium chloride in step i) is in the form of a diastereoisomeric mixture wherein the trans:cis ratio is higher than 2.3:1.

5. The process according to claim 4, wherein said N-3-hydroxypropyl-1-(R)-5'-methoxylaudanosinium chloride in step i) is in the form of a diastereoisomeric mixture having the trans:cis ratio equal to 3:1.

6. The process according to claim 1, wherein said suitable nonionic polymeric adsorbent resin insoluble in water in step iii), is a resin having a macroreticular cross-linked polymeric matrix with the following repeating unit:

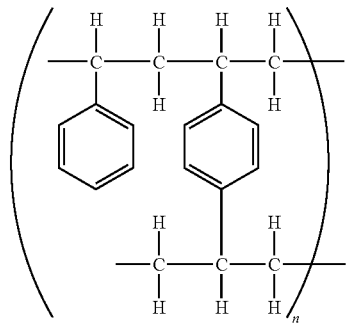

a particle mean size ranging from 0.49 to 0.69 mm, and a porosity $\geqq 0.50$ ml/ml.

7. The process according to claim 1, wherein said treatment in step iii) is carried out at room temperature.

8. The process according to claim 1, wherein said treatment in step iii) is carried out by adding said resin to said aqueous solution and maintaining the resulting mixture under stirring for a reaction time comprised between 2 and 24 hours.

9. The process according to claim 8, wherein said resin is added to said aqueous solution, at once or by portions, in a total amount comprised between 0.2 and 20 parts by weight per 1 part by weight of the starting N-3-hydroxypropyl-1-(R)-5'-methoxylaudanosinium chloride made to react in step i).

10. The process according to claim 8, wherein said resin is added to said aqueous solution by two portions staggered by 20 hours, in a total amount equal to 0.5 parts by weight per 1 part by weight of the starting N-3-hydroxypropyl-1-(R)-5'-methoxylaudanosinium chloride made to react in step i).

11. The process according to claim 1, wherein said treatment in step iii) is carried out by passing said aqueous solution through a column packed with said resin, and using water as the eluent.

12. The process according to claim 11, wherein said resin is used in an amount comprised between 10 and 40 parts by weight per 1 part by weight of the starting N-3-hydroxypropyl-1-(R)-5'-methoxylaudanosinium chloride made to react in step i).

13. The process according to claim 11, wherein said resin is used in an amount equal to 20 parts by weight per 1 part by weight of the starting N-3-hydroxypropyl-1-(R)-5'-methoxylaudanosinium chloride made to react in step i).

14. The process according to claim 1, wherein said extraction of raw mivacurium chloride in step ii) is carried out directly by adding water to the solution in said organic solvent coming from step i).

15. The process according to claim 1, wherein said extraction of raw mivacurium chloride in step ii) is carried out by evaporating said organic solvent of the solution coming from step i) to obtain an amorphous solid, which is then re-dissolved in a suitable organic solvent and the so obtained solution washed with aqueous solutions of suitable inorganic salts.

16. The process according to claim 15, wherein said suitable organic solvent is dichloromethane and said suitable inorganic salts are selected from the group consisting of sodium chloride, ammonium chloride and calcium chloride.

17. The process according to claim 1, wherein said recovery of pure mivacurium chloride in step iv) is carried out on the aqueous solution coming from step iii) by a technique selected from the group consisting of freeze-drying, spray-drying and extraction in a suitable organic solvent.

18. The process according to claim 17, wherein said extraction is carried out by first adding to said aqueous solution a suitable inorganic salt, extracting mivacurium chloride in dichloromethane, evaporating the dichloromethane obtaining an amorphous solid, dissolving said amorphous solid in methanol, evaporating the methanol obtaining an amorphous solid, and optionally adding a solvent in which mivacurium chloride is not soluble.

19. The process according to claim 18, wherein said solvent in which mivacurium chloride is not soluble is selected from the group consisting of ethyl ether, diisopropyl ether and methyl t-butyl ether.

* * * * *